(12) United States Patent
Deister et al.

(10) Patent No.: US 10,441,304 B2
(45) Date of Patent: Oct. 15, 2019

(54) SURGICAL TOOL FOR TISSUE SIZING AND TRANSECTION

(71) Applicant: AxoGen Corporation, Alachua, FL (US)

(72) Inventors: Curt Deister, Alachua, FL (US); Michael Raymond Orrico, Gainesville, FL (US); Gregory Drach, Alachua, FL (US)

(73) Assignee: AxoGen Corporation, Alachua, FL (US)

( * ) Notice: Subject to any disclaimer, the term of this patent is extended or adjusted under 35 U.S.C. 154(b) by 220 days.

(21) Appl. No.: 15/426,460

(22) Filed: Feb. 7, 2017

(65) Prior Publication Data

US 2018/0221043 A1    Aug. 9, 2018

(51) Int. Cl.
| | |
|---|---|
| *A61B 17/285* | (2006.01) |
| *A61B 17/28* | (2006.01) |
| *G01B 3/34* | (2006.01) |
| *G01B 5/08* | (2006.01) |
| *A61B 90/00* | (2016.01) |
| *A61B 17/11* | (2006.01) |
| *A61B 17/32* | (2006.01) |

(52) U.S. Cl.
CPC .............. *A61B 17/282* (2013.01); *G01B 3/34* (2013.01); *G01B 5/08* (2013.01); *A61B 17/1128* (2013.01); *A61B 2017/320052* (2013.01); *A61B 2090/061* (2016.02)

(58) Field of Classification Search
CPC . A61B 17/282; A61B 17/285; A61B 17/2926; A61B 17/2927; A61B 2017/1125; A61B 2017/1128
See application file for complete search history.

(56) References Cited

U.S. PATENT DOCUMENTS

| | | | |
|---|---|---|---|
| 3,816,919 A | 6/1974 | Portnoy | |
| 4,306,561 A * | 12/1981 | de Medinaceli ... | A61B 17/1128 606/152 |
| 4,881,550 A | 11/1989 | Kothe | |

(Continued)

FOREIGN PATENT DOCUMENTS

JP    2014-094241    5/2014

OTHER PUBLICATIONS

Wang, X. et al., "A Novel Animal Model of Partial Optic Nerve Transection Established using an optic nerve quantitative amputator," 2012, *PLoS One* 7(9): e44360 [online, article, retrieved Jan. 14, 2016] from: http://journals.plos.org/plosone/article?id=10.1371/journal.pone.0044360, pp. 1-12.

(Continued)

*Primary Examiner* — Tuan V Nguyen

(74) *Attorney, Agent, or Firm* — Heath M. Sargeant; Holland & Knight LLP

(57) ABSTRACT

A sizing forceps is provided for fixing a nerve in place, measuring the diameter of the nerve, and providing an efficient way to resect the nerve. A sizing forceps can have an upper and lower jaw with one or more aligned notches that form apertures for holding a nerve. The apertures can have predetermined sizes that can be used to measure the diameter of a nerve. A slicing slot in the upper and lower jaw allows a nerve within an aperture to be severed to obtain a non-frayed end.

14 Claims, 8 Drawing Sheets

(56) References Cited

U.S. PATENT DOCUMENTS

| | | | |
|---|---|---|---|
| 5,011,491 A | 4/1991 | Boenko et al. | |
| 5,613,976 A | 3/1997 | Agee et al. | |
| 5,618,305 A | 4/1997 | Lolagne | |
| 5,649,946 A | 7/1997 | Bramlet | |
| 6,682,542 B2 | 1/2004 | Harkrider | |
| 7,887,558 B2 | 2/2011 | Lin et al. | |
| 7,909,841 B1 | 3/2011 | Nelson | |
| 8,273,098 B2 | 9/2012 | Strickland | |
| 8,313,495 B2 | 11/2012 | Bates | |
| 8,523,892 B2 | 9/2013 | Rehnke | |
| 8,545,485 B2 | 10/2013 | Merced-O'Neill | |
| 8,808,288 B2 | 8/2014 | Reschke | |
| 8,828,000 B2 | 9/2014 | Panchbahavi | |
| 8,876,845 B2 | 11/2014 | Suddaby | |
| 2005/0209624 A1 | 9/2005 | Vijay | |
| 2006/0271080 A1 | 11/2006 | Suddaby | |
| 2008/0109021 A1 | 5/2008 | Medoff | |
| 2008/0177297 A1 | 7/2008 | Steiner et al. | |
| 2010/0145381 A1* | 6/2010 | Moon | A61B 17/282 606/207 |
| 2013/0144313 A1* | 6/2013 | Hahn | A61F 6/204 606/142 |
| 2013/0144318 A1 | 6/2013 | Dinis Carmo | |
| 2014/0121456 A1 | 5/2014 | McCormack et al. | |
| 2014/0343590 A1 | 11/2014 | Solem et al. | |

OTHER PUBLICATIONS

Conn, H., "Optic nerve clipping for hemostasis during enucleation," *Ophthalmic Surgery*, May 1981, pp. 352-354, vol. 12, No. 5, [online, article, retrieved Jan. 14, 2016] from: http://www.ncbi.nlm.nih.gov/pubmed/7266981, pp. 1-4.

Magharious, M.M. et al., "Optic Nerve Transection: A Model of Adult Neruron Apoptosis in the Central Nervous System," *Journal of Visualized Experiments*, 2011, (51): 2241. [online, article, retrieved Jan. 14, 2016] from: http://www.ncbi.nlm.nih.gov/pmc/articles/PMC3197096/, pp. 1-8.

Nerve Dissecting Scissors 4¾, Curved, Sharp/Sharp, Smooth, Product No. 47/1040, product information, [online, webpage, retrieved Jan. 14, 2016] from: http:www/sklarcorp.com/nerve-dissection-scissors-4-3-4-curved-sharp-sharp-smooth.html, pp. 1-2.

Schiedler, V. et al., "Snare Technique for Enucleation of Eyes with Advanced Retinoblastoma," *Archives of Ophthalmology*, 2007, pp. 680-683, vol. 125, No. 5, [online, article, retrieved Jan. 14, 2016] from: http://archopht.jamanetwork.com/article.aspx?articleid=419268, pp. 1-7.

Dakota Knife product information, medicaldesignsllc.com, May 23, 2013, [online, webpage, retrieved Jan. 14, 2016] from: http://medicaldesiqnsllc.com/wp-content/themes/medicaldesignstheme/images/ED0075RC_DK_brochure.pdf, pp. 1-4.

* cited by examiner

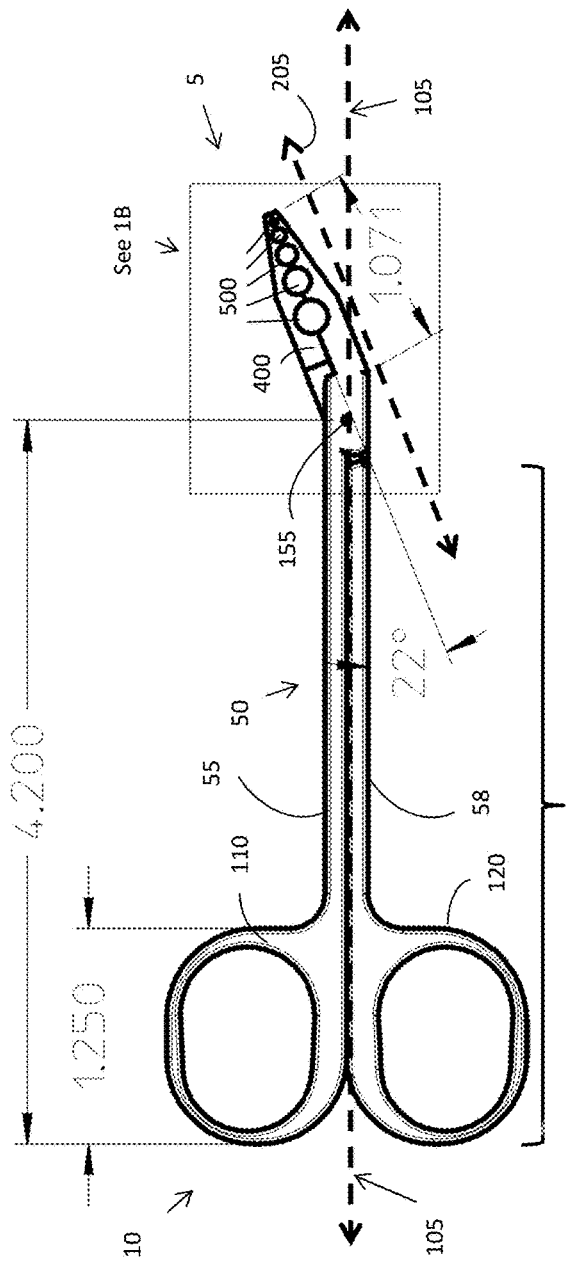
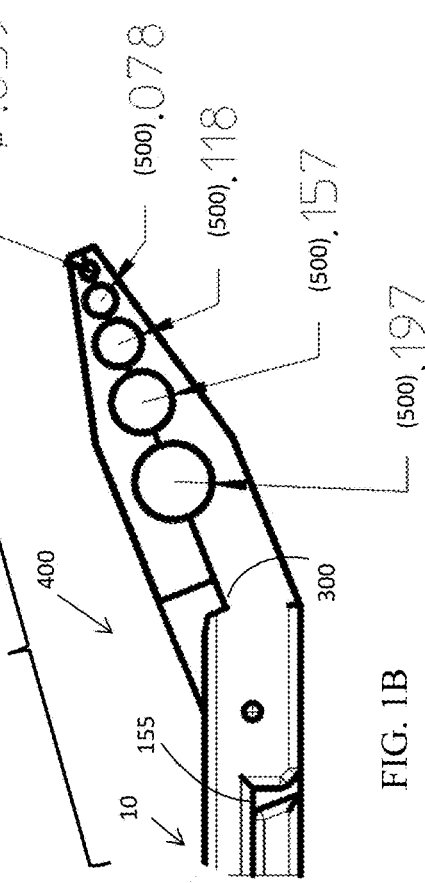
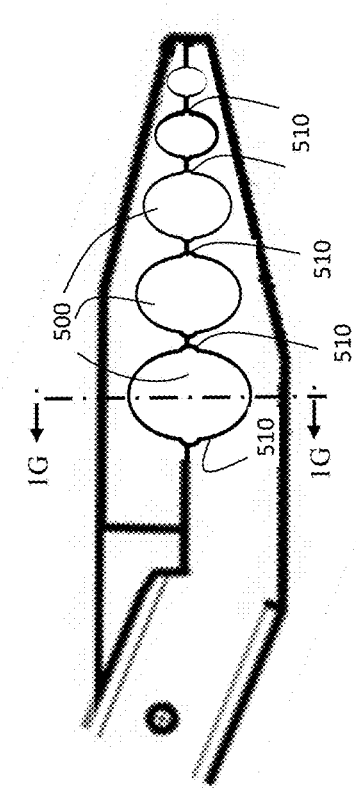
FIG. 1A
FIG. 1B
FIG. 1F

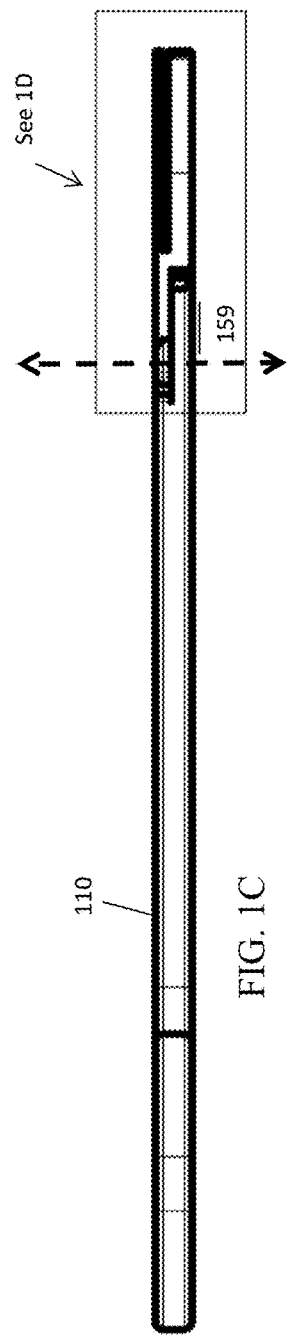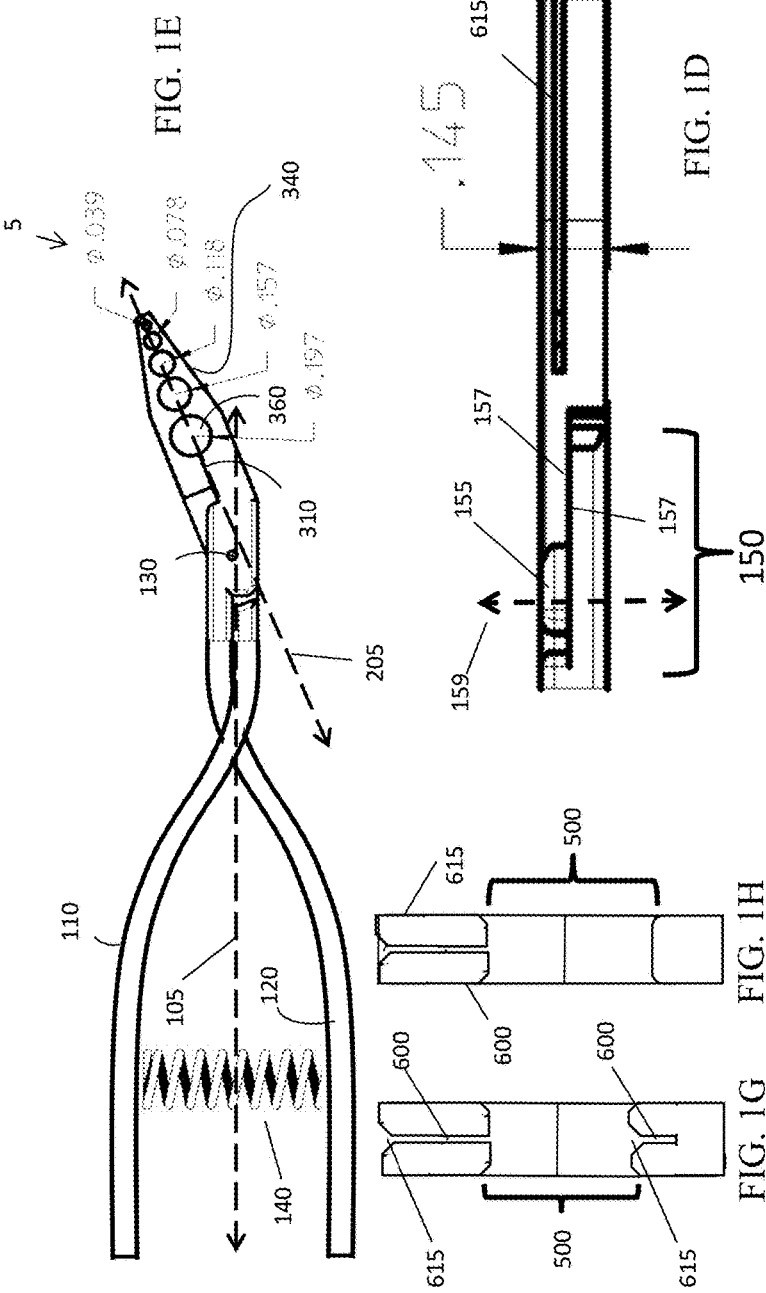

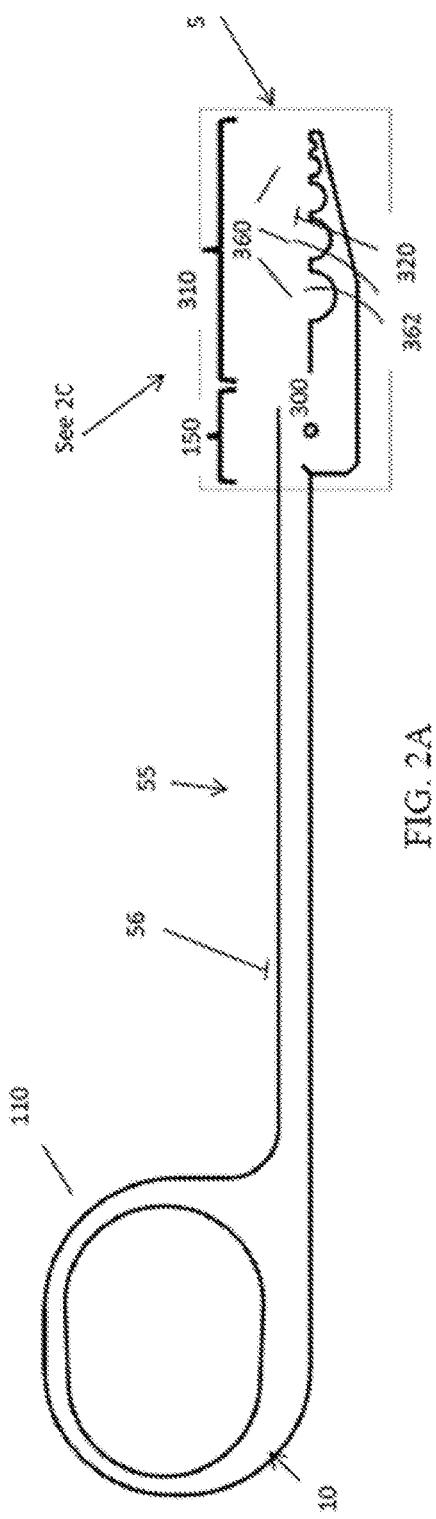
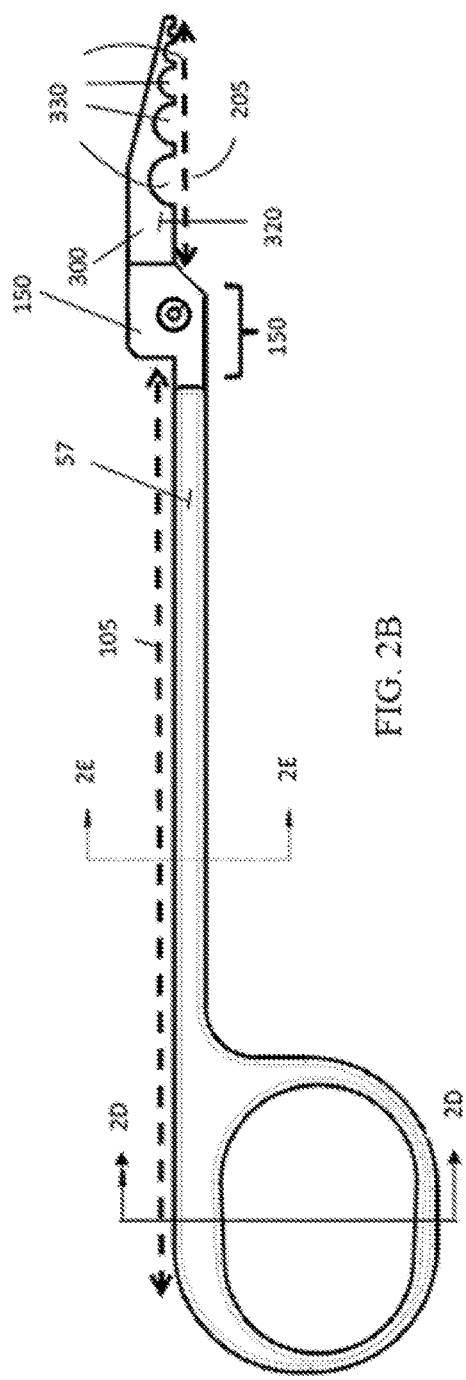
FIG. 2A
FIG. 2B

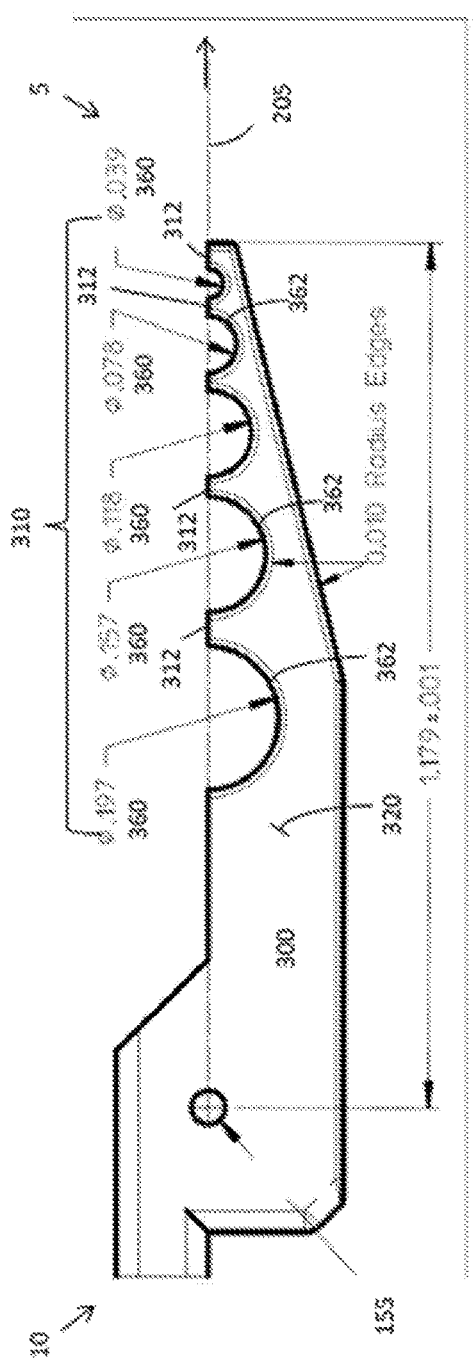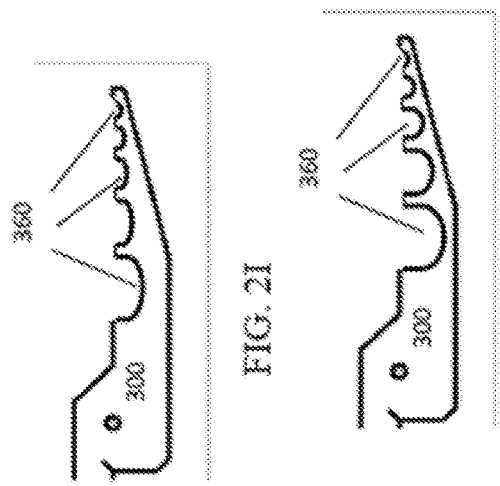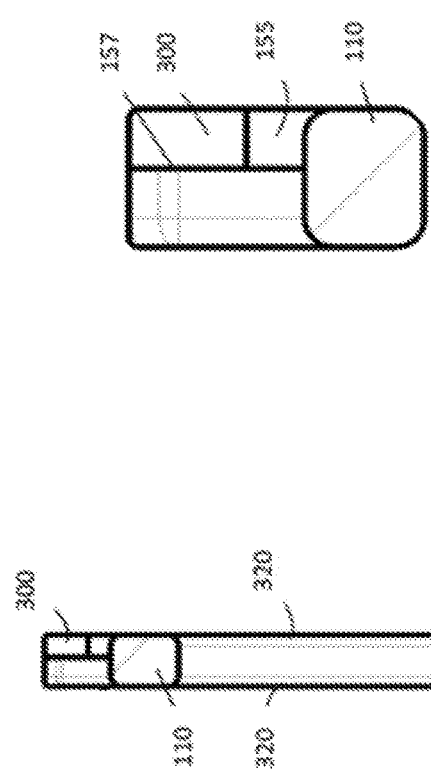

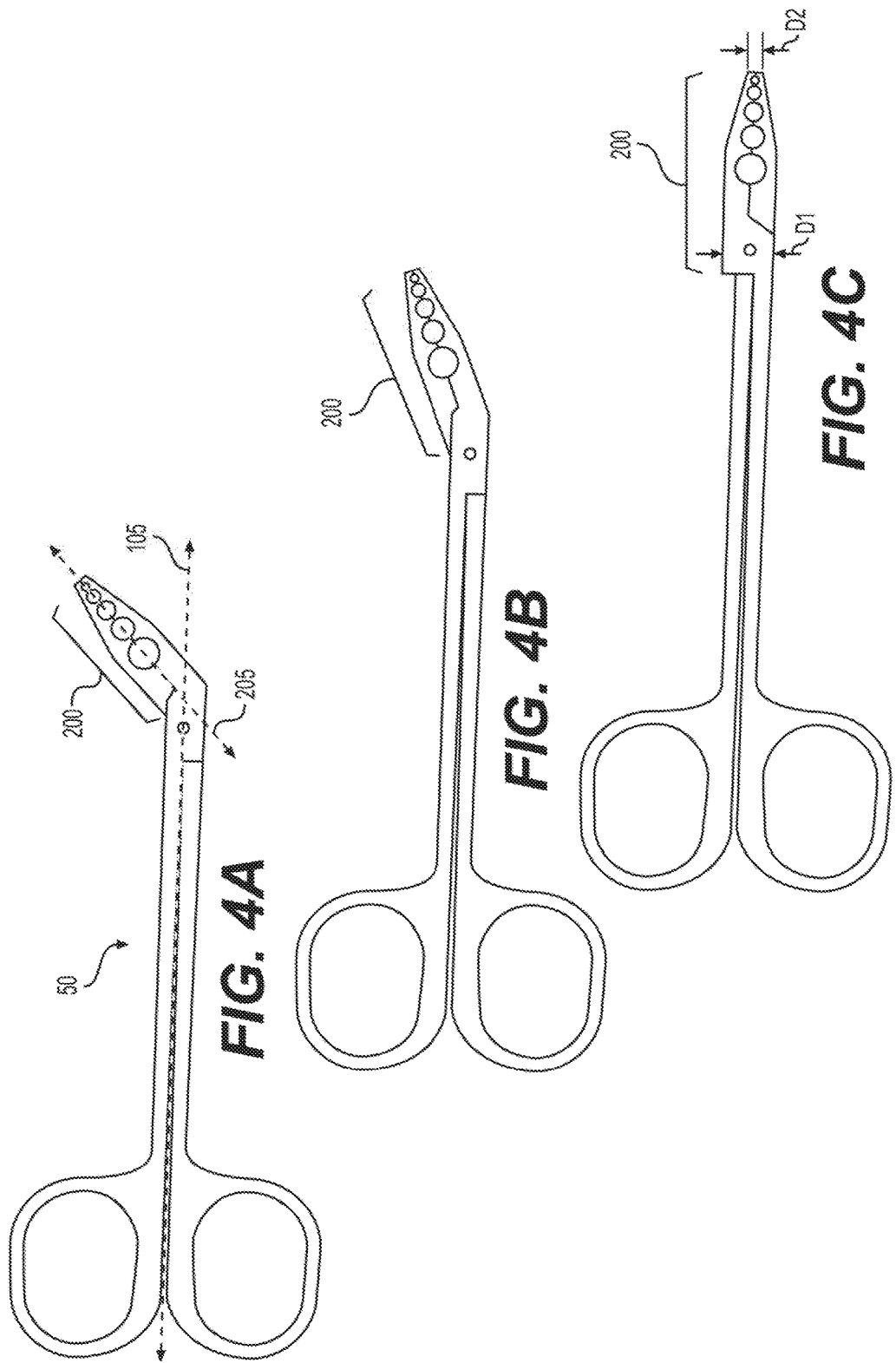

SURGICAL TOOL FOR TISSUE SIZING AND TRANSECTION

This invention was made with government support under grant no. W81XWH-13-1-0448 awarded by the U.S. Department of Defense through the office of U.S. Army Medical Command. The government has certain rights in the invention.

BACKGROUND OF INVENTION

Nerves can be transected for a variety of reasons. Whether the nerve is transected deliberately or by accident, repair of the nerve can be facilitated if a nerve end is cut and free of frayed or damaged areas, or randomly extending axons and tissue. Clean nerve ends can be easier to coapt to other nerve ends or grafts and can promote alignment of the axons from each terminal nerve end. Also, nerve ends that are to be capped or covered can be easier to manipulate and development of neuromas can be minimized if the nerve end is free of randomly extending axons.

In order to obtain a clean cut nerve end, it may be necessary to resection the nerve tissue some distance away from the terminal end, to remove damaged or non-viable tissue at the terminal nerve end. Resection of nerve tissue can be difficult. If done incorrectly it can result in a new terminal nerve end that is crushed, frayed, or that has multiple transection lines caused by the cutting implement making multiple passes or sawing across the tissue. Properly bracing the circumference of the nerve in the area of transection can minimize such damage to the one or more new terminal nerve ends. There are devices that can be used to support a nerve, while a cutting implement is used to transect the nerve. Often these devices do not entirely brace the full circumference and secure the position of the nerve, thus, allowing the nerve to roll or turn during the cutting process. This can necessitate excessive force being applied by the cutting implement in order to hold the nerve while it penetrates the tougher outer epineurium. This force can crush the softer internal nerve tissues. Alternatively, a cutting implement may have to be passed through the tissue more than once to incrementally sever the nerve tissue, which can result in a frayed nerve end.

If the resected nerve end is to be coapted to, or inserted into, a graft or implant, the nerve must be measured in vivo, so that an appropriately-sized graft can be selected. It has been demonstrated that when obtaining sizes of nerves during surgical procedures, the measurements are usually inaccurate. Nerve tissue is soft and pliable and does not often have a defined diametric shape. As such, it can be difficult to visually estimate the size of a nerve or obtain an accurate measurement of the diameter when the nerve is placed on a flat measuring surface.

Every manipulation and change of equipment or tools that must be made during surgery takes time and increases the opportunities for error. Devices and surgical tools that have multiple functions are desirable, as they can reduce the number of manipulations necessary to complete a procedure.

BRIEF SUMMARY

In accordance with the subject invention, the problem of measuring the diameter of a nerve and transecting the nerve to obtain a clean nerve end for coaptation or capping procedures is solved by the use of a single sizing forceps instrument.

The sizing forceps can surround a nerve in the area to be transected providing peripheral bracing of the nerve. The sizing forceps can also secure the position of the nerve, to minimize sliding or rolling of the nerve during the transecting process. This allows the nerve to be cut in a single stroke or at least with minimal strokes. The sizing forceps can also have multiple apertures of different diameters in the head end. The nerve diameter can be determined by selecting the appropriately sized aperture that encloses but does not pinch, constrict, or otherwise damage the nerve tissue. The correctly selected aperture can also be used to brace an area of the periphery of the nerve without crushing or damaging the nerve.

Specific embodiments of a sizing forceps have two pivoting members, each member having a handle portion and a jaw portion, where the combined jaw portions form the head end. A pivot point located between the handle portion and the jaw portions allows the pivoting members to rotate, in relation to one another, around the pivot point. The jaw portion of each pivoting member can have multiple diameter semi-circular cut-outs. When the handle portions are brought together through rotation around the pivot point, the jaw portions are simultaneously brought together so the semi-circular cut-outs are aligned to form the multiple diameter apertures in the head.

Advantageously, the jaw portions align across and make contact with surfaces between the semi-circular cut-outs on each jaw portion. This inhibits the jaw portions from coming any closer together and maintains the diameters of the multiple apertures. Thus, regardless of the amount of force applied to the handle portions, the jaw portions will maintain alignment and the prescribed aperture diameters. Chamfering of select edges can also inhibit pinching of the nerve tissue.

Once the correct aperture size has been determined and a nerve is braced and secured therein, the nerve can be cut. The blade used should be surgically sharp, straight, and free of defects on the cutting edge. The nerve can be cut by several techniques using the sizing forceps. The nerve extending out from either side of an aperture can be transected by placing the blade along an outside edge of the head end and slicing transversely across the aperture. There can also be a slicing slot within the head end. A slicing slot can longitudinally bisect the jaw portions, thereby bisecting each aperture. A blade passed through the slicing slot will cut across a nerve in one of the apertures.

The head portion can be angled or slanted on the handle portion to provide easier access to a nerve, particularly a nerve in vivo, where other tissues can obstruct access. The edges of the head portion can also be rounded, curved, flattened, or otherwise smoothed to inhibit abrasion of tissues that the head contacts.

Advantageously, the embodiments of the subject invention do not require excessive force to be applied against the jaw portions. As long as the jaw portions can be closed and their faces aligned against each other, nerve tissue within an aperture can be measured and cut. This can enable the sizing forceps to be manufactured from any of a variety of materials, including materials amenable to being disposable or recyclable.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention.

FIG. 1A is a side elevation view of a sizing forceps, according to an embodiment of the subject invention. Dimensions shown are in millimeters.

FIG. 1B is a side elevation view of the enlarged head portion of a sizing forceps, according to an embodiment of the subject invention. Dimensions shown are in millimeters.

FIG. 1C is a top plan view of the sizing forceps embodiment, shown in FIG. 1A.

FIG. 1D is top plan view of the enlarged head portion of the sizing forceps, shown in FIG. 1C. Dimensions shown are in millimeters.

FIG. 1E is side elevation view of an alternative embodiment of a sizing forceps, according to the subject invention. This embodiment has a biasing element to urge the handles apart, which holds the upper jaw and lower jaw together. Dimensions shown are in millimeters.

FIG. 1F is a side plan view of an alternative embodiment of a head portion. This embodiment illustrates one alternative shape for the apertures. Also illustrated are indented edges on interstitial faces.

FIGS. 1G and 1H are cross-sectional views taken along line 1G in FIG. 1F to illustrate an embodiment of indented edges on interstitial faces and insert ports on slicing slots.

FIG. 2A is side elevation view of the first outer side of a first member, according to one embodiment of the subject invention.

FIG. 2B is a side elevation view of the first inner side of a first member, according to one embodiment of the subject invention.

FIG. 2C is a side plan view of an enlarged head portion of a first member, according to one embodiment of the subject invention. Dimensions shown are in millimeters.

FIG. 2D is a cross-sectional view taken along line 2D in FIG. 2B.

FIG. 2E is a cross-sectional view taken along line 2E in FIG. 2B.

FIGS. 2I and 2J are enlarged side elevation views of alternative embodiments of a lower jaw of a first member, according to the subject invention. These alternative embodiments have non-circular notches.

FIGS. 4A, 4B, and 4C are photographs of embodiments of a sizing forceps, according to one embodiment of the subject invention. In FIG. 4A, the head portion is angled at about 45° relative to the handle portion. In FIG. 4B, the head portion is angled at about 22.5° relative to the handle portion. The head portion is aligned with the handle portion in FIG. 4C.

DETAILED DISCLOSURE

Figure 2F:
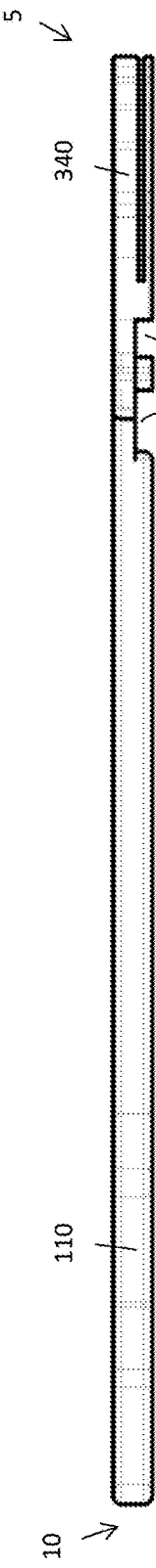
FIG. 2F is a bottom plan view of a first member, according to one embodiment of the subject invention.

The subject invention provides a surgical tool for sizing and assisting with transection or cutting of tissue. In specific embodiments, the subject invention provides sizing forceps, or similar devices, for use in measuring the diameter of a nerve and bracing and holding an area of the nerve in place for transection.

The subject invention is particularly useful in the field of surgical nerve repair, including nerve grafting or nerve coaptation procedures, where the non-viable or damaged tissue of a nerve needs to be removed prior to a procedure.

In the description that follows, a number of terms used with regard to surgical repair of tissues are utilized. In order to provide a clear and consistent understanding of the specification and claims, including the scope to be given such terms, the following definitions are provided.

The terms "nerve" and "nerve tissue" as used herein are merely for literary convenience. The embodiments of the subject invention are not limited to use with only nerve tissue and can be utilized with other tissues, such as, for example, blood vessels and tendons.

Further, reference is made throughout the application to the "proximal end" and "distal end." As used herein, the proximal end is that end placed nearest to the nerve tissue or the patient during use. For example, the head portion is at the proximal end of the sizing forceps. Conversely, the distal end of the device is that end closest to the surgeon during use. For example, the handle portion is at the distal end of the sizing forceps.

As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen in FIGS. 1A and 1B that a sizing forceps 50 of the subject invention comprises first member 55 and a second member 58, each having a handle portion 100 with a proximal end 5 and a distal end 10. At the proximal end of the handle portion of each member there are attached a lower jaw 300 and an upper jaw 400 that are cooperatively engaged to come together and form a head portion 200 with one or more apertures 500 for receiving a nerve without pinching, constricting, or otherwise damaging the nerve tissue. Each of these general components can have one or more sub-components, which will be discussed in detail below.

The first member 55 and the second member 58 can be joined so that they can be simultaneously manipulated to control the opening and closing of the handle portion 100 and the head portion 200. In one embodiment, the first member has a first handle 110 and a lower jaw 300 and the second member 58 has a second handle 120 and an upper jaw 400. In an alternative embodiment, the first member has a first handle 110 and an upper jaw 400 and the second member 120 has a second handle and a lower jaw 300. As will be discussed below, a biasing member can be utilized to hold the handles together or apart, which can determine whether the jaws are maintained in an opened or closed position. A person with skill in the art would be able to determine the appropriate arrangement of the handles and the jaws and whether a biasing element is required. Such variations are within the scope of this invention.

The first member has a first outer side 56 from the handle portion to the head portion. The first member also has a first inner side 57 that extends from the handle portion to the head portion, but includes a joint area 150 between the handle portion and the head portion, at which the first member rotates against the second member. Likewise, the second member 58 has second outer side 59 from the handle portion to the head portion. The second member also has a second inner side 60 that extends from the handle portion to the head portion, but includes a joint area 150 between the handle portion and the head portion, at which the second member rotates against the first member.

Figure 3A:
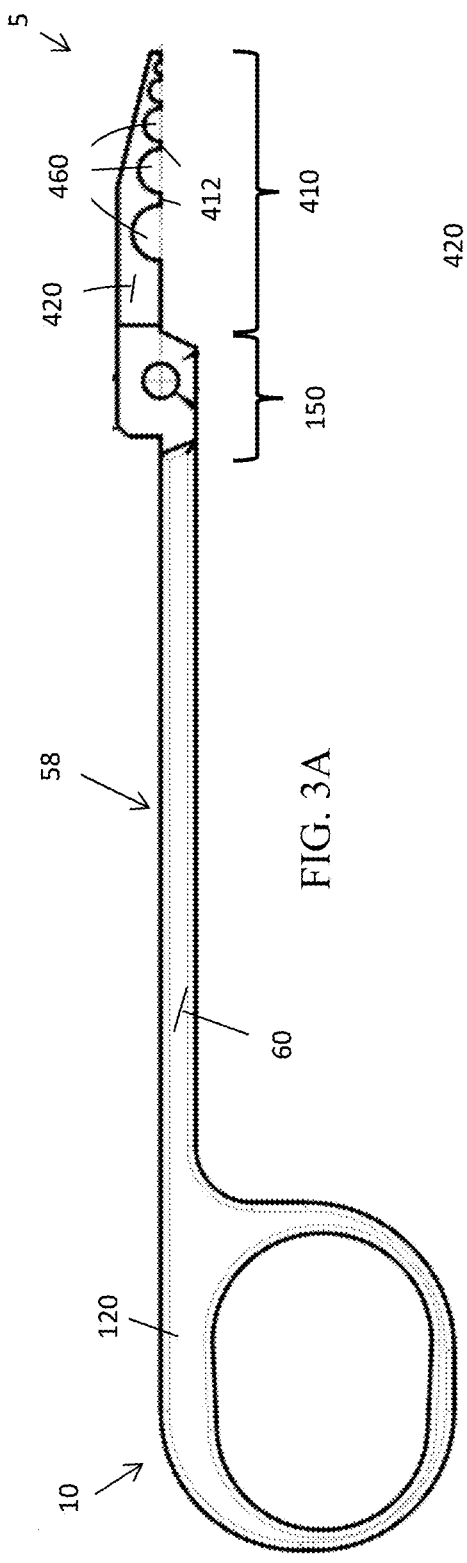
FIG. 3A is a side elevation view of the second outer side of a second member, according to one embodiment of the subject invention.
Figure 5:
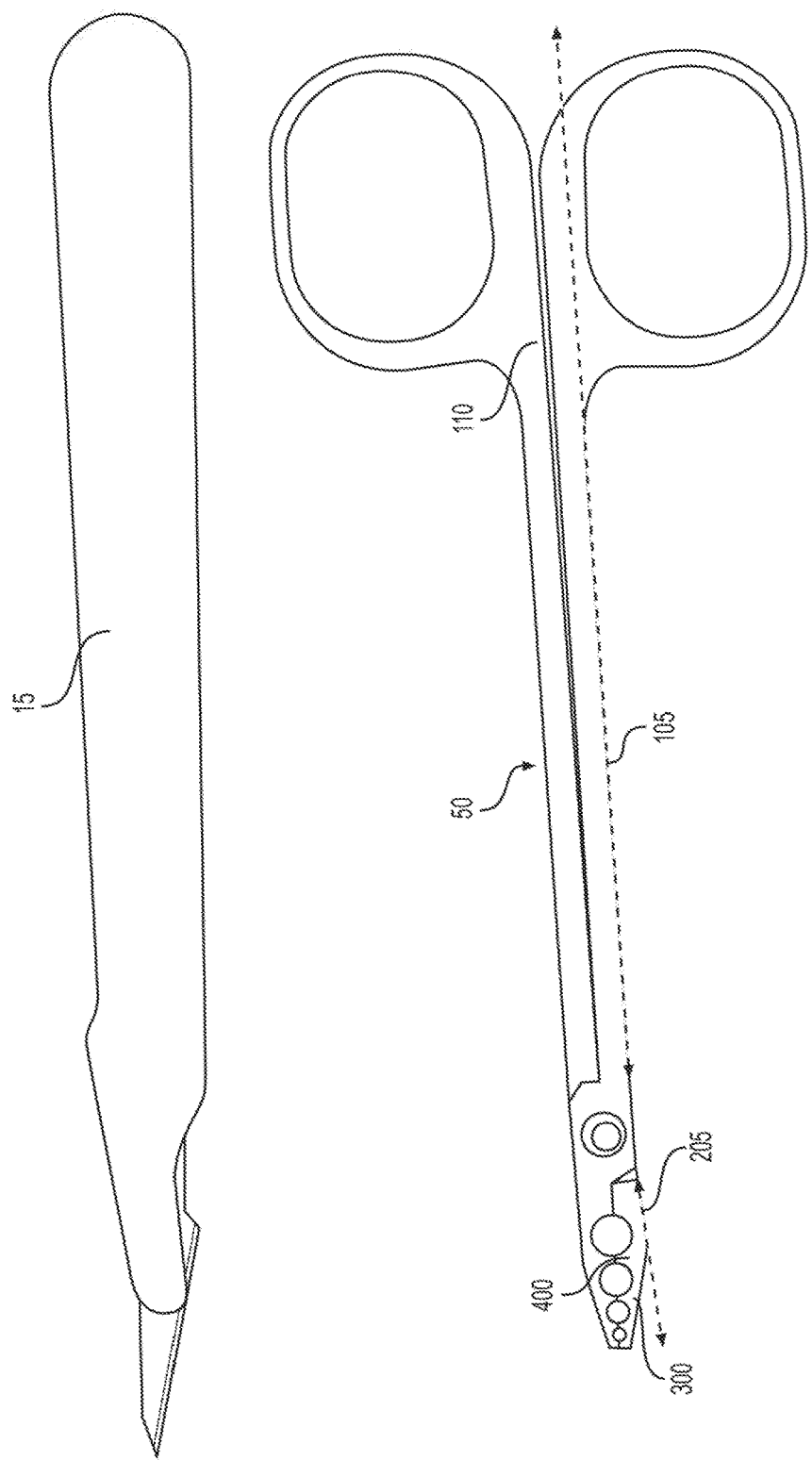
FIG. 5 illustrates a sizing forceps and a cutting implement that can be used therewith.

When the first member 55 and the second member 58 are rotatably connected, as discussed below, the first handle 110 and the second handle 120 constitute the handle portion 100 that can be manipulated to bring the lower jaw 300 and the upper jaw 400 together. In one embodiment, the handle portion has a scissors-like configuration, as shown for example, in FIGS. 1A and 5. This embodiment has a first handle 110, to which the lower jaw 300 can be attached, and a second handle 120, to which the upper jaw 400 can be attached, the members being configured as left and right symmetrical with each other and pivotally attached by a joint member 155 at their proximal ends 5. Joint members are known in the art and allow rotation about a common axis 159, as shown, for example, in FIG. 1C. When the first handle and second handle are squeezed together, along a longitudinal line 105, which is illustrated in FIGS. 2A and 3A, the motion can bring the lower jaw and upper jaw, at the proximal ends of the respective members, into contact. FIGS. 1A and 5 show non-limiting examples of an embodiment where the handle members come together at the longitudinal line 105.

In another embodiment, the first handle 110 and the second handle 120 are pivotally connected with a joint member 155 at their proximal ends 5 and are urged apart by a compression spring or other biasing member 140. It can be beneficial for the handle members of the handle portion 100 to be curved, as shown, for example, in FIG. 1E, to facilitate rotation of the handle portions and the jaws. The upper jaw and lower jaw can be connected to the first handle and second handle, respectively, such that when the handle members are squeezed towards each other, or towards the longitudinal line 105 of the handle portion, the jaws are separated. When the members are not squeezed, the biasing member forces the handle members apart, which brings the jaws together, as shown for example in FIG. 1E. Other handle types could also be utilized. Thus, any configuration of the handle portion 100 that provides control over the opening and closing of the upper jaw and lower jaw is within the scope of this invention.

When the first member 55 and the second member 58 are rotatably connected, the lower jaw 300 and the upper jaw 400 constitute a head portion 200. In general, the head portion 200 can operate in tandem with the handle members, as discussed above, so that the jaws can come together along all or at least some portion of the lengthwise extent 205 of the head portion. Preferably, the jaws do not cross or pass each other, but are aligned along the lengthwise extent. FIGS. 1A, 1E, and 4A illustrate examples of the lengthwise extent 205 of a head portion. The alignment of the head portion 200 relative to the handle portion 100 can be variable, to accommodate use of the sizing forceps 50 in different situations. In one embodiment, the head portion can be aligned with the handle portion, such that the longitudinal line 105 of the handle portion is coplanar, collinear, or otherwise in-line with the lengthwise extent 205 of the head portion. FIGS. 2B, 3B, 4C, and 5 illustrate non-limiting examples of this embodiment.

In another embodiment, the head portion 200 is angled relative to the handle portion 100, such that the lengthwise extent 205 of the head portion is angled or bent relative to the longitudinal line 105 of the handle portion. FIGS. 1A, 2B, 3B, and 4A illustrate non-limiting examples of this embodiment. In one embodiment, the head portion is angled, relative to the handle portion, between approximately 10° and approximately 60°. In a particular embodiment, the head portion is angled, relative to the handle portion, between approximately 20° and approximately 50°. In one specific embodiment, the head portion is angled, relative to the handle portion, at approximately 22°, one example of which is shown in FIGS. 1A and 4B. In another specific embodiment, the head portion is angled, relative to the handle portion, at approximately 45°, which is shown, by way of example in FIG. 4A. The ability to determine alternative angles for the head portion is within the capability of one of ordinary skill in the art and such variations are within the scope of this invention.

When placing the head portion around a nerve, the jaws are separated by the handle members and the lower jaw can be positioned approximately perpendicular to the length of the nerve and slid around the nerve so that the nerve is between the upper jaw and the lower jaw. The shape of the upper and/or the lower jaw can facilitate the procedure of sliding the jaw around the nerve. In one embodiment, the edges and surfaces of the upper and lower jaws are beveled or smoothed to reduce sharp or rough edges and encourage sliding of the nerve over those surfaces. In a further embodiment, the upper jaw and lower jaw are tapered towards the proximal end 5, so that the proximal end of the head portion 200 is narrower or has a smaller diameter than the distal end of the head portion. By way of example, FIG. 4C shows a first diameter, $D_1$, at the distal end 10 of the head portion and a second diameter, $D_2$, at the terminal proximal end 5 of the head portion. It can be seen that, in this example, $D_1$ is larger than $D_2$, indicating a smaller diameter at the proximal end. Alternatively, the diameter of D1 and D2 are the same or approximately the same.

Figure 2G:
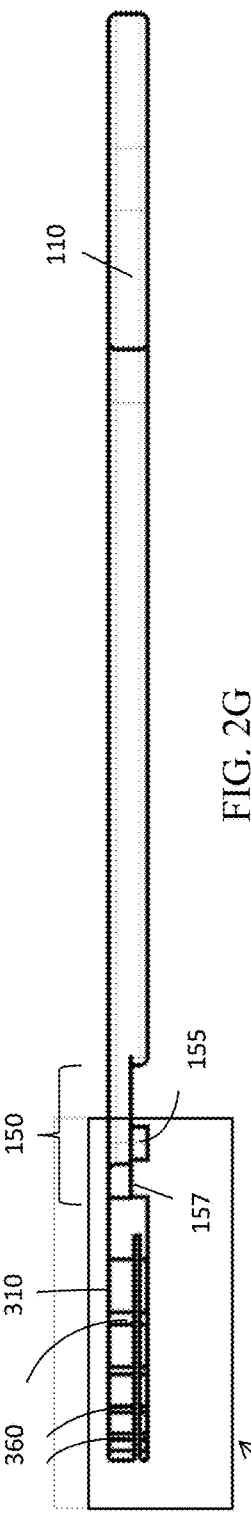
FIG. 2G is a top plan view of a first member, according to one embodiment of the subject invention.

The boundary that separates the head portion 200 and handle portion 100 can be the joint area 150. In one embodiment, the joint area comprises two surfaces 157, which are located on the first inner side 57 of the first member 55 and the second inner side 60 of the second member 58. The joint area can also include a joint member 155, which can be on either or both surfaces, that rotatably connects the handle members 110 and 120, where the handle portions come together at the common axis 159 to rotate against each other. FIG. 1D shows a non-limiting example of a joint area. In one embodiment, the surfaces 157 are recessed or narrower than the handle and the jaws, as shown, for example, in FIGS. 2F and 2G. The narrowness allows the handle members and upper and lower jaws to overlap, when the handle members are connected by the joint member 155 at the common axis 159. The recessed surface can extend out from the joint member a sufficient distance to allow the handle members and jaws to rotate without being impinged upon by material or surfaces around the recessed surface. The use of a joint area and a joint member to form a pivotal connection is known in the art. A person having skill in the art will be able to determine the appropriate dimensions for recessed surface that will allow proper rotation around the joint member. Such variations in the configuration of a joint area are within the scope of the subject invention.

As mentioned previously, the head portion 200 includes the lower jaw 300 and the upper jaw 400, which pivot by the rotation of their respective handle members on a joint member 155. While the invention is described herein with reference to the upper jaw and the lower jaw, it should be understood that these terms are not intended to confer any order or specific placement in structural orientation. The upper jaw could just as readily be used in a position below or to the side of the lower jaw described herein, and vice versa. Thus, reference to upper jaw and lower jaw are for descriptive purposes and are not intended to limit the invention or its use in any way.

In one embodiment, the lower jaw 300 has a first face 310 and at least one notch 360 within the first face. In one embodiment, the first face is a substantially flat surface, whereby an imaginary plane across the flat surface will be parallel to the lengthwise extent 205, as shown, for example, in FIGS. 2A and 2B. This can urge the lower jaw and the upper jaw to align with each other, as shown in the example in FIGS. 1B and 5. The flat alignment of the upper and lower jaw can also inhibit one or the other jaw from sliding past the other if excessive force is applied to the handle members.

Figure 2H:
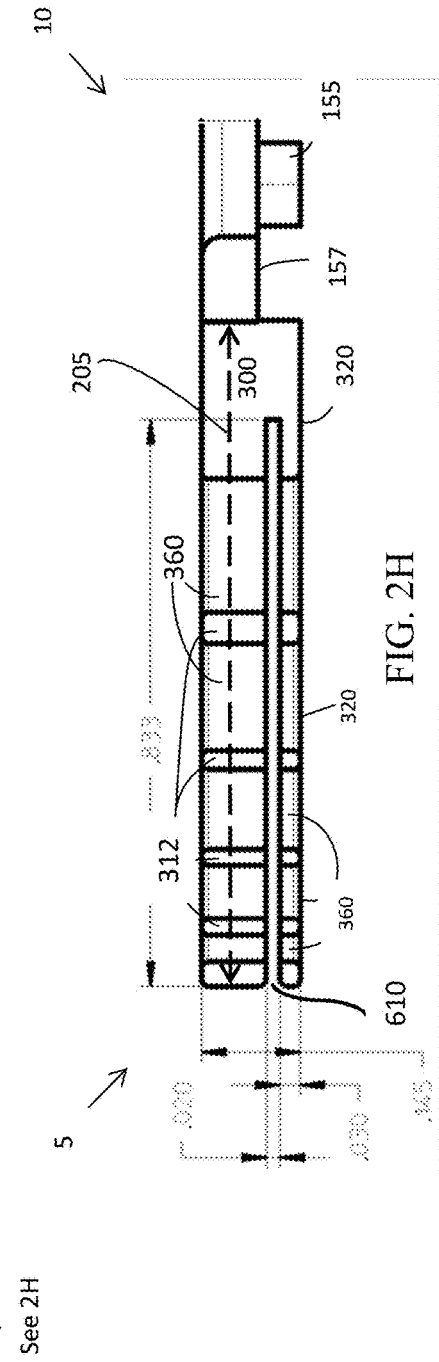
FIG. 2H is a top plan view of an enlarged head portion of a first member, according to one embodiment of the subject invention. Dimensions shown are in millimeters.

In a further embodiment, the first face is interrupted by at least one notch 360 that is cut, molded, or otherwise formed transverse to the lengthwise extent 205 of the lower jaw, such that the notch further opens onto the side edges 320 of the jaw, which is shown, for example, in FIGS. 2C and 2H. In other words, the at least one notch can be perpendicular to the lengthwise extent. The at least one notch within the lower jaw opens onto the first face, which breaks or divides the first face into smaller interstitial faces 312. In a further embodiment, there are two or more notches 360 within the lower jaw. In a specific embodiment, there are five notches within the lower jaw that interrupt the first face, wherein the notches open onto the first face, forming multiple interstitial faces 312, as shown, for example, in FIG. 2C.

The at least one notch in the lower jaw can have any circumferential shape. Multiple notches in a lower jaw could also have different circumferential shapes. It can be preferable, though not required, for the shape to be curved, which can be more conforming to the shape of a nerve and beneficial for cutting. In one embodiment, the notches are substantially semi-circular, as shown by way of example in FIGS. 2A and 2C. In another embodiment, the notches are semi-oval, or U-shaped, wherein the long axis can be either parallel or perpendicular to the lengthwise extent 205, as shown in the example in FIGS. 1F and 2I. In yet another embodiment, the notches are semi-ovate, such as shown, for example, in FIG. 2J. Other curved shapes could also be used, including but not limited to, semi-ovate, multi-curved or waved, hyperbolic, or other curved or semi-curved forms.

In another embodiment, the circumferential shape of a notch has at least one straight side. By way of example, a notch could have an arch-type circumference, where the sides are parallel and straight and the bottom or closed end 362 is rounded. A notch could also be square or rectangular, where there are no curved edges. Furthermore, the notches can have the same or different circumferential shapes.

In another embodiment, the lower jaw has two or more notches, each of different size diameters. In a specific embodiment, shown, by way of example, in FIGS. 2A and 2H, the lower jaw has five notches 360, which open onto the first face 310 and side edges 320. In a further specific embodiment, the notches have a semi-circular circumferential shape and are graduated in size from the largest at the distal end 10 of the lower jaw to the smallest size at the proximal end 5 of the lower jaw. In one embodiment, the diameters of the notches range from between approximately 0.03 inch to approximately 0.2 inch. In one specific embodiment, the diameters of the semi-circular notches are approximately 0.197", 0.157", 0.118", 0.078" and 0.039", an example of which is shown in FIG. 1B. Alternatively, a specific embodiment has notches ranging in size from approximately 1 mm, approximately 2 mm, approximately 3 mm, approximately 4 mm, and approximately 5 mm.

In a further embodiment, a notch 360 has a beveled, chamfered, filleted, sloping, or smoothed edge where it opens onto the side edge 320. This can inhibit fraying, cutting or other injury to a tissue positioned across the notch.

When the first handle 110 of the handle portion 100 is joined to the second handle 120 of the handle portion at the joint area 150, the upper jaw 400 can aligned with the lower jaw. FIGS. 1A, 4A-4C, and 5 illustrate the alignment of the upper jaw with the lower jaw. In one embodiment, the upper jaw 400 has a second face 410 and at least one pairing notch 460 within the second face. In one embodiment, the first face is a substantially flat surface, whereby an imaginary plane across the flat surface will be parallel to the lengthwise extent 205, as shown, for example, in FIGS. 3A and 3B. As mentioned above, this can urge the upper jaw and the low jaw to align with each other. This can also direct force applied to the handle member to the first face 310 and the second face 410, whereby the flat surfaces and the alignment of the upper and lower jaw can inhibit one or the other jaw from sliding past the other if excessive force is applied to the handle members.

Figure 3C:
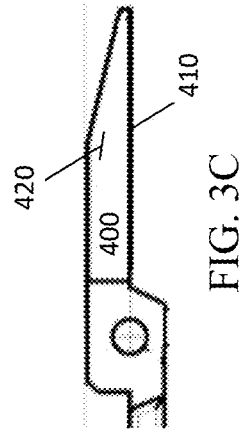
FIG. 3C is an enlarged side elevation view of an alternative embodiment of an upper jaw of a second member, according to the subject invention. This alternative embodiment does not utilize pairing notches.
Figure 3B:
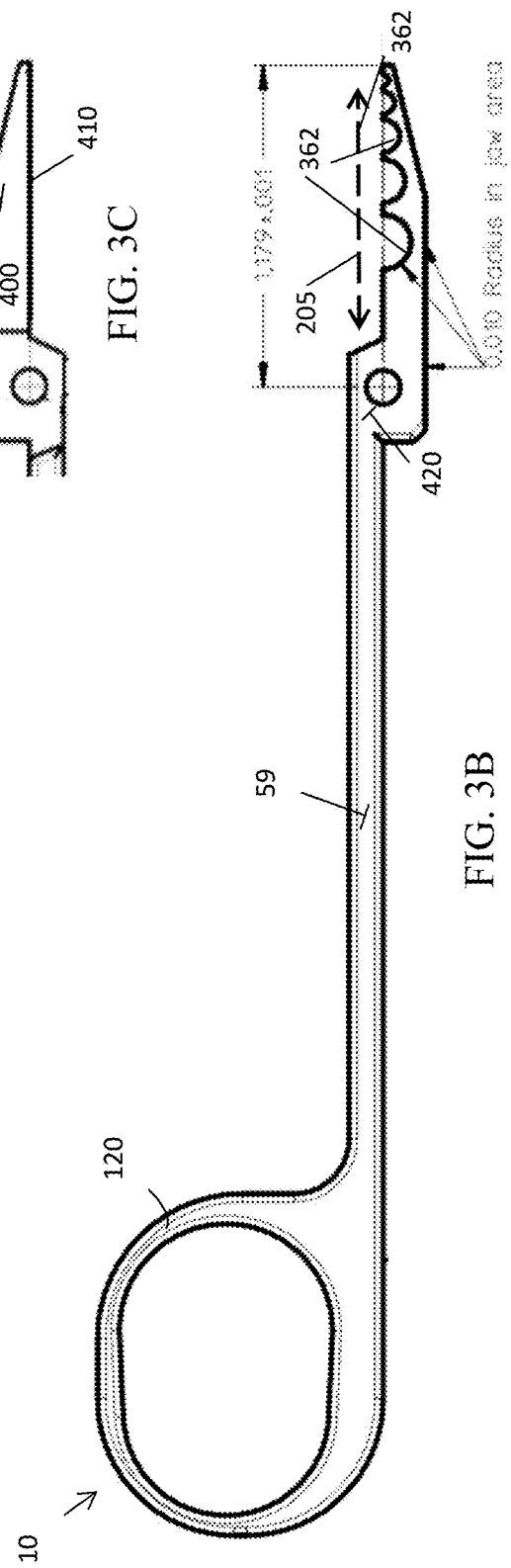
FIG. 3B is a side elevation view of the second inner side of a second member, according to one embodiment of the subject invention. Dimensions shown are in millimeters.

In a further embodiment, the second face 410, similarly to the first face 310, is interrupted by at least one pairing notch 460 that is cut, molded or otherwise formed to be transverse to the lengthwise extent 205 of the lower jaw, such that the pairing notch further opens onto the side edges 420 of the jaw, which is shown, for example, in FIGS. 3A and 3B. In other words, the at least one pairing notch can be perpendicular to the lengthwise extent. The at least one pairing notch within the upper jaw opens onto the second face, which breaks or divides the second face into smaller second interstitial faces 412. In a further embodiment, there are two or more pairing notches 460 within the lower jaw. In a specific embodiment, there are five notches within the upper jaw that interrupt the second face, wherein the notches open onto the second face, forming multiple second interstitial faces 412, as shown, for example, in FIG. 3A. In one embodiment, when the lower jaw 300 is aligned with the upper jaw 400, as discussed above, the interstitial faces 312 of the first face can align with the interstitial faces 412 of the second face 410. In a further embodiment, the notches 360 in the lower jaw will align with or "pair-up" with the pairing notches 460 in the upper jaw, to form apertures 500 within the head portion. The nerve tissue within an aperture can be supported while held in place for transecting. Furthermore, selecting the correct aperture size can also help determine the diameter of the nerve tissue.

As with the lower jaw, the at least one pairing notch in the upper jaw can have any circumferential shape. Ideally, the circumferential shape of a pairing notch can complement, cooperate with, or otherwise be operable with a notch 360 it pairs with in the lower jaw. Multiple pairing notches in the upper jaw could also have different circumferential shape. It can be preferable, though not required, for the circumferential shape to be curved, which can be more conforming to the shape of a nerve and beneficial for cutting. The circumferential shapes that can be utilized for a notch 360 in a lower jaw 300 have been discussed above and are reasserted here with regard to the circumferential shapes of a pairing notch 460 in an upper jaw.

In another embodiment, the upper jaw has two or more notches, each of different size diameters. In a specific embodiment, shown, by way of example, in FIGS. 3A and 3B, the upper jaw 400 has five pairing notches 460, which open onto the first face 410 and side edges 420. In a further specific embodiment, the pairing notches have a semicircular circumferential shape and are graduated in size from the largest at distal end 10 of the upper jaw to the smallest size at the proximal end 5 of the upper jaw. In still further specific embodiment, the pairing notches 460 align with the notches 360 to form circular apertures, as shown, for example, in FIGS. 1B and 1E. In one embodiment, the diameters of the pairing notches range from between approximately 0.03 inch to approximately 0.2 inch. In one specific embodiment, the diameters of the semi-circular notches are approximately 0.197", 0.157", 0.118", 0.078" and 0.039." Alternatively, a specific embodiment has notches ranging in size from approximately 1 mm, approximately 2 mm, approximately 3 mm, approximately 4 mm, and approximately 5 mm.

In a further embodiment, a pairing notch 460 has a beveled, chamfered, filleted, sloping or smoothed edge where it opens onto the side edge 320. This can inhibit fraying, cutting or other injury to a tissue positioned across the pairing notch or within an aperture.

In another embodiment, the upper jaw 400 can have a second face 410, but not have pairing notches. This provides for a smooth, continuous second face that can be aligned with the interstitial faces 312 of the first face 310. FIG. 3C illustrates one non-limiting example of an upper jaw without pairing notches. With this embodiment, the side edges 420 of the second face of the upper jaw can be aligned with the side edges 320 of the lower jaw. As with the pairing notches, the side edges at or near the second face can be beveled, chamfered, filleted, sloped, or smoothed to inhibit injury to a tissue that it contacts. The second face 410 can be positioned over the notches 360 within the lower jaw without concern for precise alignment with the notches. This embodiment can be advantageous for sizing forceps 50 intended for repeated use and sterilization. Over time, any surgical tool can experience wear from use and repeated sterilization. With this embodiment, the sizing forceps can have a longer usable life, as long as the upper jaw 400 and the lower jaw 300 can be sufficiently aligned.

The lower jaw 300 and the upper jaw 400 together form the head portion 200 of a sizing forceps 50. When the jaws are brought together, the interstitial faces 312 and the second interstitial faces 412 come together and there is formed at least one aperture 500 within the head portion. Preferably, there is more than one aperture in a head portion, where the apertures have different diameters. FIGS. 4A, 4B, and 4C illustrate one embodiment of a sizing forceps having five apertures of graduated sizes. Different diameters of nerve tissue can be secured and held in place by using the correct size aperture.

When the interstitial faces 312 and the second interstitial faces 412 come together, they can form a seal between the apertures 500 in the head portion 200. To inhibit tissue within the apertures from becoming pinched between the interstitial faces, the edges of the interstitial faces within the apertures can be indented, such that they have a chamfered, beveled, filleted, sloped, or otherwise recede from the aperture. The indented edges 510 can inhibit tissue within the aperture from being pinched when the interstitial faces come together. FIG. 1F illustrates a non-limiting embodiment of interstitial faces with indented edges 510.

When nerve grafts are being implanted, it can be necessary to select a graft having a diameter similar to the in vivo nerve end. It has been shown that visual size determinations are often incorrect. Utilizing measuring devices with a flat surface, such as rulers, also does not give an accurate measurement of diameter. With a sizing forceps of the subject invention, the sizes or diameters of the apertures can be used to measure the diameter of a nerve placed therein.

The head portion can have a plurality of apertures 500 that can be used to measure the diameter of a nerve. Each aperture can open onto the side edges of the upper jaw and lower jaw, such that the direction of an aperture is transverse to the lengthwise extent 205 of the lower jaw. In one embodiment, a head portion has between two and eight apertures where the apertures have diameters that range from between approximately 0.01 inch to approximately 0.3 inch. In a further embodiment, a head portion has between three and seven apertures, where the apertures have diameters that range between approximately 0.01 inch and approximately 0.3 inch. In a still further embodiment, a head portion has between four and six apertures, where the diameters of the apertures range between approximately 0.01 inch and approximately 0.3 inch. In a particular embodiment, the head portion has five apertures, where the apertures have diameters that range from between approximately 0.03 inch to approximately 0.2 inch. In one specific embodiment, the head portion has five apertures, where the diameters of the apertures 500 are approximately 0.197", 0.157", 0.118", 0.078" and 0.039." Alternatively, a specific embodiment has notches ranging in diameter from approximately 1 mm, approximately 2 mm, approximately 3 mm, approximately 4 mm, and approximately 5 mm and any diameter in a range between any two of the listed diameters.

There are many situations in which a nerve has to be cut or severed. It may be necessary to remove tissue from a nerve end to reach viable, vascularized tissue or a section of nerve may need to be removed from one area to be coapted to a nerve in another area. Regardless of the reason, the method by which the nerve is severed can affect the success of the procedure and the quality of healing and regeneration of nerve tissue. The sizing forceps of the subject invention can be helpful in providing support to a nerve by holding it within an aperture. When the nerve tissue is to be severed, the cutting implement can be placed along one of the side edges and slid along the side edge to provide a clean, precise cut across the nerve.

In one embodiment, the head portion has a slicing slot 600 through which a cutting implement 15, such as, for example, a surgical grade safety blade or scalpel, such as, by way of example, the one shown in FIG. 4, can be passed through to sever a nerve at a point within an aperture. In one embodiment, the lower jaw 300 is traversed by a first part 610 of the slicing slot that bisects the notches, as shown, for example, in FIG. 2H. In a further embodiment, the upper jaw 400 is traversed by a second part 620 of the slicing slot that bisects the pairing notches. When the upper jaw and lower jaw are rotated and the faces aligned, as described above, the first part of the slicing slot and the second part of the slicing slot are also aligned to create a full slicing slot through the head portion.

A slicing slot can extend through the head portion, in the same direction as the lengthwise extent 205. In one embodiment, the slicing slot extends through the head portion in a direction transverse to the direction of the notches 360 and the pairing notches 460, discussed above. The slicing slot can extend through the head portion, going through the upper jaw 400 and the lower jaw 300, and opening onto the proximal end 5 of the upper jaw and the lower jaw. FIG. 1D illustrates an example of this embodiment. In a further embodiment, the length of a slicing slot, in the direction of the lengthwise extent 205, is between approximately 0.8" and 1.0" and the width of a slicing slot, in a direction transverse to the lengthwise extent, is between approximately 0.015" and approximately 0.025." Furthermore, the width of a slicing slot, in a direction perpendicular to the lengthwise extent, can be between approximately 0.03" and approximately 0.01". In a specific embodiment, the length of a slicing slot is approximately 0.833" and the width of a slicing slot is approximately 0.02".

In an alternative embodiment, the slicing slot 600 extends entirely through the upper jaw 400, but terminates within the lower jaw 300 at a point below the notches 360. Thus, with this embodiment, the slicing slot does not extend through the entire head portion 200. Specifically, it does not extend entirely through the lower jaw. In one embodiment, the slicing slot terminates at the bottom or closed end 362 of the notches. In another embodiment, the slicing slot terminates beyond the closed end of the notches, such that a cutting implement 15 will pass entirely through one or more notches in the lower jaw. In one embodiment, the slicing slot terminates between approximately 0.005" and approximately 0.001" below the closed end of one or more notches.

The nerve tissue within an aperture 500 can be supported along the length of the aperture. The slicing slot 600 can be advantageously narrow, providing only sufficient space for a cutting implement to pass through the slicing slot in the upper jaw and, possibly, the lower jaw. To facilitate insertion of a cutting implement, an insert port 615 can be fashioned on the outside of the upper jaw 400. The insert port can be a shallow, depressed area on either side of the outside of the sliding slot that is wider than the slicing slot. The insert port can be used to guide or direct a cutting implement into the slicing slot. In one embodiment, the edges of the insert port are chamfered, beveled, filleted, sloped, or otherwise wider than the remaining length of the slicing slot. The insert port can extend along all or at least some part of the length of the slicing slot. FIG. 1G is a cross-sectional view, taken along line 1G in FIG. 1F, showing an insert port 615 that is wider than the slicing slot. FIG. 1H is a similar cross-sectional view showing that the insert port may not extend along the entire length of the slicing slot.

The slicing slot can extend into the lower jaw, such that it bisects the lower jaw or, alternatively, terminates just below the notches in the lower jaw. In a further embodiment, the slicing slot in the lower jaw can also have an insert port 615, similar to that in the upper jaw. FIG. 1G illustrates a non-limiting example of a lower jaw having an insert port. The insert port in the lower jaw can provide additional guidance to a cutting implement as it traverses through an aperture 500.

These features of a slicing slot allow the nerve to be cut anywhere along the aperture and obtain a non-frayed end. In one embodiment, the slicing slot is centered between the side edges 320 of the lower jaw and the side edges 420 of the upper jaw 400. In an alternative embodiment, the slicing slot is off-center between the side edges 320 of the lower jaw and the side edges 420 of the upper jaw, an example, of which, is shown in FIG. 1D.

Surgical procedures involving nerve tissue can obtain improved results if viable, healthy nerve tissue is used. This can necessitate incrementally removing non-viable or unhealthy nerve tissue. When removing nerve tissue, obtaining a clean, non-frayed nerve end for use can improve procedure outcomes and provide better healing. If nerve grafts are being utilized, it can be preferable for the graft and the nerve being repaired to have similar diameters. The sizing forceps embodiments of the subject invention provide an effective method for fixing a nerve in place, measuring the diameter of the nerve, and providing an efficient and effective procedure for cutting nerve tissue to provide a non-frayed end.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for measuring the diameter of a nerve tissue, the method comprising:
   A. manipulating a sizing forceps around the periphery of a nerve tissue with an upper jaw and a lower jaw separated, wherein the sizing forceps comprise:
      a first member having:
         a first handle portion with a first outer side and a first inner side,
         the lower jaw at one end of the first handle portion with a first face,
         one or more notches within the lower jaw, where the notches open onto the first face, the first outer side and the first inner side;
      a second member having:
         a second handle portion with a second outer side and a second inner side,
         the upper jaw at one end of the second handle portion with a second face,
         one or more pairing notches within the upper jaw, where the pairing notches open onto the second face, the second outer side and the second inner side; and
      a joint area at which the first handle portion is rotatably connected to the second handle portion;
      such that the handle portions, when manipulated along a longitudinal extent to rotate at the joint area, bring the lower jaw into alignment with the upper jaw, along a lengthwise extent, so that the first face is against the second face, thereby forming a head portion in which the notches and pairing notches come into alignment so as to form one or more apertures within the head portion;

B. positioning the nerve tissue into at least one of the one or more notches in the lower jaw or into at least one of the one or more pairing notches in the upper jaw;

C. manipulating the handle portions to bring the lower jaw and the upper jaw closer together, so as to begin forming an aperture;

D. determining, as the aperture forms, if the nerve tissue diameter matches the diameter of the forming aperture; and E. repeating steps A-D until an appropriately sized aperture is formed around the nerve tissue.

2. The method, according to claim 1, wherein the one or more apertures have different diameters.

3. The method, according to claim 2, wherein the one or more apertures decrease in size.

4. The method, according to claim 1, wherein the head portion of the sizing forceps comprises a slicing slot within the head portion that is transverse to the one or more apertures.

5. The method, according to claim 4, wherein the width of the slicing slot is sufficient that a surgical cutting blade can pass through the slicing slot.

6. The method, according to claim 5, wherein the width of the slicing slot is between approximately 0.03" and approximately 0.01".

7. The method, according to claim 5, wherein the width of the slicing slot is approximately 0.020 inch.

8. The method, according to claim 4, wherein the lengthwise extent of the head portion of the sizing forceps is at least one of coplanar, collinear, or in-line with the longitudinal extent of the handle portions.

9. The method, according to claim 4, wherein the lengthwise extent of the head portion of the sizing forceps is at an angle with the longitudinal extent at between approximately 10° and approximately 60°.

10. The method, according to claim 4, wherein the lengthwise extent of the head portion of the sizing forceps is at an angle with the longitudinal extent at between approximately 20° and approximately 50°.

11. The method, according to claim 4, wherein the lengthwise extent of the head portion of the sizing forceps is at an angle of approximately 22° with the longitudinal extent.

12. The method, according to claim 4, wherein the lengthwise extent of the head portion of the sizing forceps is at an angle of approximately 45° with the longitudinal extent.

13. The method, according to claim 4, wherein the head portion of the sizing forceps has multiple apertures with different diameters, and wherein the method further comprises positioning the nerve tissue into one or more of the apertures to determine the correct size aperture for securing, supporting, and measuring the diameter of the nerve tissue.

14. The method, according to claim 4, wherein the method further comprises passing a cutting implement through the slicing slot to transect the nerve tissue positioned within the one or more apertures.

* * * * *